(12) United States Patent
Coppola et al.

(10) Patent No.: US 8,785,370 B2
(45) Date of Patent: *Jul. 22, 2014

(54) REACTIVE KERATIN PROTEIN FORMULATIONS AND METHODS OF USING FOR REVITALIZING HAIR

(75) Inventors: Peter Coppola, Boca Raton, FL (US); Vito C. Bucario, Boca Raton, FL (US)

(73) Assignee: Keratin Complex Holdings, Inc. (VG)

( * ) Notice: Subject to any disclaimer, the term of this patent is extended or adjusted under 35 U.S.C. 154(b) by 0 days.

This patent is subject to a terminal disclaimer.

(21) Appl. No.: 12/421,601

(22) Filed: Apr. 9, 2009

(65) Prior Publication Data

US 2009/0211593 A1 Aug. 27, 2009

Related U.S. Application Data

(63) Continuation-in-part of application No. 11/973,059, filed on Oct. 5, 2007.

(60) Provisional application No. 61/163,815, filed on Mar. 26, 2009.

(51) Int. Cl.
*A61K 38/00* (2006.01)
*A61K 38/17* (2006.01)

(52) U.S. Cl.
USPC .......................................... 514/1.1; 530/357

(58) Field of Classification Search
None
See application file for complete search history.

(56) References Cited

U.S. PATENT DOCUMENTS

| | | |
|---|---|---|
| 2,261,094 A | 10/1941 | Bamber |
| 2,267,741 A | 12/1941 | Langbein |
| 3,071,515 A | 1/1963 | Wehr |
| 3,519,383 A | 7/1970 | Peters |
| 3,842,848 A | 10/1974 | Karjala |
| 3,919,265 A | 11/1975 | Bugaut |
| 4,023,926 A | 5/1977 | Bugaut |
| 4,041,150 A | 8/1977 | Karjala |
| 4,279,996 A | 7/1981 | Yoshioka |
| 4,530,829 A | 7/1985 | Abe |
| 4,659,566 A | 4/1987 | Petrow |
| 4,719,099 A | 1/1988 | Grollier |
| 4,773,912 A | 9/1988 | Nordmann |
| 4,774,075 A | 9/1988 | Lang |
| 4,818,520 A | 4/1989 | Fleischner |
| 4,840,791 A | 6/1989 | Matthews |
| 4,992,267 A | 2/1991 | DenBeste |
| 5,148,822 A | 9/1992 | Akhtar |
| 5,437,860 A | 8/1995 | Jarvis |
| 5,460,967 A | 10/1995 | Fink |
| 5,540,910 A | 7/1996 | Samain |
| 5,651,961 A | 7/1997 | Neill |
| 5,679,329 A | 10/1997 | Dupuis |
| 6,306,377 B1 | 10/2001 | Coppola |
| 6,316,598 B1 | 11/2001 | Van Dyke et al. |
| 7,148,327 B2 | 12/2006 | Kelly |
| 8,414,872 B2 * | 4/2013 | Resnick et al. .............. 424/70.2 |
| 2001/0006664 A1 | 7/2001 | Ensley |
| 2001/0047082 A1 | 11/2001 | Van Dyke |
| 2003/0012758 A1 | 1/2003 | Jourdan et al. |
| 2003/0106564 A1 | 6/2003 | Olshavsky |
| 2003/0118537 A1 * | 6/2003 | Devin-Baudoin et al. ... 424/70.2 |
| 2003/0236253 A1 | 12/2003 | Chizh et al. |
| 2005/0013786 A1 | 1/2005 | Sabbagh |
| 2005/0129644 A1 * | 6/2005 | Sabbagh et al. ............. 424/70.2 |
| 2005/0226838 A1 | 10/2005 | Krause et al. |
| 2005/0226839 A1 | 10/2005 | Huang et al. |
| 2006/0104928 A1 | 5/2006 | Furtado |
| 2007/0020215 A1 | 1/2007 | Mathonneau |
| 2009/0126756 A1 | 5/2009 | Syed |

FOREIGN PATENT DOCUMENTS

| | | |
|---|---|---|
| FR | 2547728 | 12/1984 |
| GB | 526289 A1 | 9/1940 |
| GB | 860978 A1 | 2/1971 |
| JP | 11139940 A1 | 5/1999 |
| WO | WO/99/47107 A1 | 3/1999 |
| WO | WO/2006/121700 A2 | 11/2006 |
| WO | WO/2007/032762 A1 | 3/2007 |
| WO | WO/2007/135298 A1 | 11/2007 |
| WO | WO/2009/000057 A1 | 12/2008 |

OTHER PUBLICATIONS

EWG An Environmental Working Group (EWG) Investigation: Hair Straightener Makers and Salons Cover Up Dangers: Flat Out Risky—About the Brand: Coppola—Copomon Enterprises, LLC, (http://www.ewg.org/hair-straighteners/our-report/see-the-brands/index.html@bb_comp_id=7.html.*

OSHA "USDept. of Labor's OSHA cites Florida manufacturers and distributors of hair products containing formaldehyde for health violations Companies failed to protect workers, warn product users of hazards"; Region 4 News Release: 11-1314-ATL (431) Sep. 8, 2011; http://www.osha.gov/pls/oshaweb/owadisp.show_document?p_table=NEWS_RELEASES&p_id=20640.*

Edwin R. Theis, "The Collagen-Quinone Reaction. I. Fixation and Thermolability as a Function of pH Values," J. Biol. Chem. 157:23-33 (1945). Online at http://www.jbc.org/cgi/reprint/157/1/23.pdf. PDF attached.

(Continued)

*Primary Examiner* — Maury Audet
(74) *Attorney, Agent, or Firm* — Thompson Hine L.L.P.

(57) ABSTRACT

A formulation is disclosed comprising a reactive keratin derivative. Also described are methods of making the formulation and hair treatment methods and systems that include use of the formulation. The hair treatment methods may be useful, for example, in straightening or revitalizing hair.

14 Claims, 12 Drawing Sheets

(56) References Cited

OTHER PUBLICATIONS

Roland G. Kallen, "Mechanism of reactions involving Schiff base intermediates. Thiazolidine formation from L-cysteine and formaldehyde," J. Am. Chem. Soc., 1971, 93 (23), pp. 6236-6248. Online at http://pubs.acs.org/doi/pdf/10.1021/ja00752a040. DOI: 10.1021/ja00752a040. PDF attached.

Caribbean Dream Relaxer, http://caribbeandreamrelaxer.com/compare.html, as viewed Feb. 19, 2009. PDF printout attached.

Alexandra Drosu, "Brazilian hair straighteners offer formaldehyde-free products," LA Times, AUg. 176, 2008, http://articles.latimes.com/2008/aug/17/image/ig-beauty17, as viewed Nov. 5, 2008. PDF attached.

"Brazilian Keratin Straightening—One of the best hair straightening treatments around," http://www.abcarticledirectory.com/Article/Brazilian-Keratin-Straightening—One-of-the-best-hair-straightening-treatments-around/177961. PDF attached. Viewed Oct. 30, 2008.

C.B. Anfinsen, M. L. Anson, W. E. Hill, Advances in Protein Chemistry, New York: Academic Press, 1965, pp. 304-306. ISBN 0120342022, 9780120342020. Excerpt from pp. 304-306 attached from Google Books, http://tinyurl.com/lct6mo, as viewed Jun. 15, 2009.

Max Feughelman, "Mechanical properties and structure of alpha-keratin fibres: wool, human hair and related fibres," Sydney, Australia: UNSW Press, 1997, pp. 109-110. Excerpt attached from Google Books (see http://tinyurl.com/nr5ybf), as viewed Jun. 15, 2009.

J.D. Smyth and D.P. McManus, "The Physiology and Biochemistry of Cestodes," Cambridge University Press, 1989 ISBN 0521355575, 9780521355575, p. 173. Excerpt from p. 173 taken from Google Books, http://tinyurl.com/memnkd, as viewed Jun. 15, 2009.

Public sale of Keratin Complex product began Oct. 7, 2007, with a composition related to the materials of the patent application and those of the priority documents (U.S. Appl. Nos. 11/973,059 and 61/163,815). There was also experimental use of related materials from Aug. 2007 to Oct. 2007.

PATBASE.com, translation of abstract of JP11139940A (above), accessed Dec. 3, 2010.

Ratner, S. et al., "The Action of Formaldehyde Upon Cysteine," 7 pages (1937).

Schubert, M.P., "Compounds of Thiol Acids With Aldehydes," 10 pages (1936).

English translation of FR 2547728, published Dec. 28, 1984.

Full statement of Larry Solomon, of Keratin Complex, dated Oct. 15, 2010, titled "Differences of Keratin Complex".

Weber, H.U. et al., "Thiazolidine-4-carboxylic acid, a physiologic sulfhydryl antioxidant with potential value in geriatric medicine," Arch. Gerontol. Geriatr., 1 (1982) 299-310.

\* cited by examiner

```
30
 ↓
┌─────────────────────────┐
│ Keratin film protein    │─32
│ is synthesized.         │
└─────────────────────────┘
            ⇓
┌─────────────────────────┐
│ Keratin film protein is heated │─34
│ and vaporized to a fine mist.  │
└─────────────────────────┘
            ⇓
┌─────────────────────────┐
│ Vaporized keratin is           │
│ hydrolized with high current in │─36
│ water.                          │
└─────────────────────────┘
            ⇓
┌─────────────────────────────────┐
│ 6-7% of keratinized water is fed to │
│ a filter to sift very fine proteins in │
│ the high molecular range 12000-  │─38
│ 19000 Daltons.                   │
└─────────────────────────────────┘
```

*Fig. 2*

| Coppola Hair Treatment Formula A | |
|---|---|
| Ingredient | Measured in 1 kg of solution |
| Ti5 Trionic Modified Kerato-Protein Complex. | 39.45 |
| Water | 49.3 |
| Aminopropyl Phenyl Trimethicone | 1.7 |
| Vitamin E- oil | 0.1 |
| aldehydes | 1.1 |
| Poly-glycereal-laurate 10 | .25 |
| Cyclomethicone-dimethicone | 3.7 |
| Guar Gum extract | 1.80 |
| Trace Iron-Oxide catalyst | .5 |
| Trace Methanol | .5 |
| Benzoquinone Disulphide | .5 |
| Fragrance | 1.1 |
| | 100% |

*Fig. 4*

| Formulation component (or treatment) | Action | % increase in weight of hair fiber | Torsional enhancement after treatment (ratio before and after) |
|---|---|---|---|
| Keratin Ti5 Sulfhydril Groups on Hair keratin | Forms a chain between the hair and the keratin protein in the formulation | 2% | .072 |
| Benzoquinone | May reduce water intake by attaching reactive keratin protein onto open damaged hair shaft sites. $RSCH_2OH + RSH \rightarrow RSCH_2SR + H_2O$ (release from hair fiber by heat). | 1.5% | 0.17 |
| Cyclo-Dimethicone | Seals hair during repair and acts to give a shine by filling in spectral gaps on hair shaft after treatment. | 0.05% | 0 |
| Aldehydes+Trace Iron Oxide + Trace methanol | Reacts to bind to hair cuticle by forming methylinic bridges between sulfhydril groups. | .02% | .08 |
| Hot iron application | Temperatures greater than 350°F. | -2.5% | .175 |

*Fig. 7*

| Coppola Hair Treatment Formula B for badly damaged hair | Weight Percent |
|---|---|
| Ingredient | 0 |
| Ki5 Trionic kerato protein | 51.0 |
| Water | 37.0 |
| Aminopropyl Phenyl Trimethicone | 4.0 |
| Vitamin E- oil | 1.5 |
| Grapeseed extract | 1.0 |
| Poly-glycereal-laurate | 0.50 |
| Cyclomethicone-dimethicone | 2.00 |
| Alcohol | 1.30 |
| Guam extract | 1.5 |
| Fragrance | 0.2 |
| Totals | 100% |

| Coppola Hair Treatment Formula C for virgin untreated hair | Wt % |
|---|---|
| Ingredient | 0.0 |
| Ki5 Trionic kerato-protein | 35.0 |
| Water | 57.9 |
| Jojoba oil | 0 |
| Vitamin E oil | 1.0 |
| Grapeseed extract | 0 |
| Poly-glycereal-laurate 10 | .1 |
| Aminopropyl Phenyl Trimethicone | 1.0 |
| Alcohol | 0.0 |
| Guam extract | 1.0 |
| Fragrance | .1 |
| Formol | 3.9 |
| Totals | 100% |

REACTIVE KERATIN PROTEIN FORMULATIONS AND METHODS OF USING FOR REVITALIZING HAIR

CLAIM TO PRIORITY

This application is a Continuation-in-Part of U.S. patent application Ser. No. 11/973,059, "Treatment Method for Revitalizing Hair and Method of Producing Keratin Protein Treatment Solution," filed Oct. 5, 2007, and also claims priority to provisional U.S. Patent Appl. Ser. No. 61/163,815, "Reactive Keratin Protein Formulations and Methods of Using for Revitalizing Hair," filed Mar. 26, 2009, both of which are hereby incorporated by reference in their entireties for all purposes.

BACKGROUND

1. Field of the Invention

This invention pertains to hair treatment methods and formulations for hair treatment.

2. Description of Related Art

Current hair revitalizing and treatment systems involve harsh chemicals, such as oxidizing agents, high concentrations for formaldehyde and other dangerous chemicals to bind conditioning agents to the hair cuticle. Prior approaches generally require the treatment carriers to first scar the cuticle and then penetrate deeply into the hair shaft, whereupon the reactive agents then substitute some of the conditioning reagents into the hair shaft through the cuticle. Over time, the cortical cells get damaged by these chemicals and then the micro-filaments may die. While these prior treatments seem to produce desirable results that may gratify some clients, eventually the damage to the hair tends to become evident and generally irreversible. The reactive component of the conditioning treatment may become less efficacious over time, and the hair of the client will deteriorate leaving a scarred and damaged hair shaft that requires even further treatment.

Also, when a high concentration of formol is used, the reagents polymerize upon heating the hair with a hot iron, sealing some of the un-reacted agents into the hair shaft for long periods of time. This is unfortunate since the hair appears healthy and shinny upon application of these harsh chemicals, but in fact is slowly being damaged over time. The precursor agents that existing treatments use must diffuse deeply into the hair to destroy the intrinsic melanin deposits. Repeated use of harsh chemicals tends to damage the hair significantly. Scalp exposure to the chemicals also may induce allergic reactions in sensitive individuals. Many hair stylists become ill from excessive exposure to the harsh ingredients used by existing hair straightening treatments. One treatment method often referred to as the Japanese treatment, for example, relies on lye and other harsh chemicals, while another treatment often called the Brazilian hair treatment uses high levels of formaldehyde in at least some versions. Alternative treatment methods are needed that produce excellent results without damage to the hair or the use of elevated concentrations of harsh chemicals.

For hair straightening, relaxers for hair are known but generally comprise harsh chemicals such as guanidine hydroxide, ammonium thioglycolate, and sodium hydroxide (lye). There is a need for hair straightening systems with reduced thioglycolates levels and that do not require elevated pH levels.

SUMMARY OF THE INVENTION

The present invention provides a system and formulation to assist in repairing damaged hair and, in some embodiments, in thermal straightening of hair. The formulation comprises an effective amount of an ionized reactive keratin derivative in an aqueous solution, said keratin derivative comprising a plurality of aldehyde groups or other reactive groups, the ionized keratin having a molecular weight between about 12,000 and 19,000 daltons, the formulation further comprising an amino-functional silicone compound, one or more additional conditioning agents, and an oxidizer suitable for promoting oxidation of sulfur groups in hair to form disulphide bridges. Other stabilizers, fragrances, coloring agents, and the like may be present. Substantially formol-free aldehyde compositions may be used to both provide fragrance and assist in desirable reactions with the hair of the subject according to the treatments methods of the present invention. The treatment methods generally comprise substantially uniform application of a formulation of the present invention to the hair of a subject, followed by elevating the temperature of the formulation on the hair by, for example, use of a hot hair iron, followed by removal of excess formulation.

In one embodiment, the reactive keratin derivative is formed by reaction of formol with keratin protein. Without wishing to be bound by theory, it is believed that the reaction of formol with keratin protein in the presence of a suitable catalyst and at a suitable temperature yields a plurality of thiazolidine groups on the keratin protein by reduction of cysteine groups, wherein the disulphide bond in the cysteine group is reduced. See, for example, Roland G. Kallen, "Mechanism of reactions involving Schiff base intermediates. Thiazolidine formation from L-cysteine and formaldehyde," *J. Am. Chem. Soc.*, November 1971, 93 (23), pp 6236-6248, http://pubs.acs.org/doi/abs/10.1021/ja00752a040 (DOI: 10.1021/ja00752a040).

Without wishing to be bound by theory, it is believed that the thiazolidine groups and perhaps remaining disulphide groups in the ionized keratin, sulfonic groups, or other sulfur-containing groups in the ionized keratin can subsequently react with cysteine groups in hair to reduce the disulphide bond, thereby relaxing the hair as part of a straightening process, if desired.

In some embodiments, the reactive ionized keratin derivative comprises a plurality of reactive groups on the keratin molecule formed by prior reaction of the keratin with a low-molecular weight aldehyde such as formol or glutaraldehyde or with other suitable aldehydes. Without wishing to be bound by theory, it is believed that in one embodiment, treatment of soluble, ionized keratin with formol attaches $-CH_2OH$ groups to sulfur on the keratin backbone, which in turn can react with other sulfur groups on other keratin molecules to form methylenic bridges between keratin molecules instead of disulfide bonds, via reactions of the form $RSCH_2OH + RSH \rightarrow RSCH_2SR + H_2O$.

In some embodiments, the reactive ionized keratin derivative may comprise a plurality of sulfonated groups (i.e., the keratin in this case may be an S-sulfonated keratin) which can then participate in reducing disulphide groups in the keratin on hair or participate in other reactions relevant to the present invention. Other ionic sulfur groups or nitrogen groups may be present on the ionized keratin molecule in various embodiments of the present invention.

The keratin used in preparing the reactive ionized keratin derivative may be derived from wool such as alpine wool. The keratin may be hydrolyzed to form a soluble keratin, which may be ionized by passing electrical current through a fine mist of keratin solution to create an ionized form of keratin. The ionized keratin may then be further reacted with aldehydes in the presence of a suitable catalyst to provide a plurality of reactive functional groups on the keratin molecule that can subsequently react with human hair or other hair, as desired. The aldehydes that are added in preparing the reactive ionized keratin may be provided with small amounts of methanol or other alcohols which may be fully or partially removed subsequently, or may remain at least in part in the formulation. The oxidizer may comprise benzoquinone such as p-benzoquinone or o-benzoquinone, niquine, peroxides, and the like.

The thickening agent may be a gum such as a cationic gum, including cationic guar gum and the like. The kinematic viscosity of the formulation, as measured with a Brookfield viscometer at 60 rpm and at 25° C., may be between about 2000 and about 5000 centistokes. The dynamic viscosity may be between about 2000 and about 5000 centipoise.

In another aspect, the present invention comprises a method for producing a treatment formulation for repairing damaged hair, comprising:
a) preparing an aqueous mixture comprising keratin protein;
b) hydrolyzing the keratin in the aqueous mixture with electrical current to create an ionized keratin solution;
c) adding an effective amount of an aldehyde composition, a thickening agent and a substantially formol-free cross-linking agent to form a first phase;
d) preparing a second phase comprising an amine-functionalized silicone and one or more conditioning agents added to water;
e) blending the first phase with the second phase.

Distilled water, including deionized distilled water, may be used as the water source for both the first phase and the second phase. The method may further comprise boiling or heat treating the ionized keratin solution to kill microbes. The combination of components to form the first phase may occur in a sealed chamber to eliminate the presence of air, or may occur under an oxygen free atmosphere. In one embodiment, the boiled or heat-treated ionic keratin solution is placed in an air-free chamber, and then the oxidizer and other non-silicone ingredients may then be slowly stirred in or added using other means. The second phase may have substantially more water than the first phase. Thus, the fraction of the water in the final product that is initially provided in the second phase may be greater than about 50%, about 60%, about 70%, about 80%, or about 90%, such as from about 80% to about 95%. In one embodiment, the water for the second phase is heated in a vessel, to which a heated silicone conditioner agent such as cyclo-dimethicone is added. The amine-functionalized silicone agent may be added simultaneously, previously, or afterwards and may also be heated or premised with other agents, as desired. In one embodiment, the amine-functionalized silicone is aminopropyl phenyl trimethicone, and the other additives blended into the second phase include poly-glyceryl laurate 10, jojoba oil extract, and vitamin E, all of which is fully blended to form the second phase. The blending of the second phase with the first phase may be done by gradually adding either of the two phases to the other at an elevated temperature (e.g., from 30° C. to 95° C., from about 40° C. to about 80° C., or greater than 40° C.), followed by cooling to room temperature and packaging of the product (in either order).

The method may further include forming a mist of droplets from the aqueous mixture of keratin protein prior to hydrolyzing the keratin, and wherein hydrolyzing the keratin with electrical current comprises applying an electrical discharge across a chamber comprising the mist of droplets. The electrical discharge may, for example, include a current of about 200 amps per cubic meter with voltage (e.g., 5V to 5000V, or more specifically 100V to 500V) and exposure times (e.g., 1 sec to 50 sec, or about 2 sec to about 10 sec) suitable to create ionized keratin proteins that are water soluble. In some embodiments, however, the production of mist may not be required, and in such cases, formation of soluble keratin may be conducted in a bulk liquid phase and may include application of electrical current or other known methods for solubilizing proteins.

In several embodiments, the formulation comprises a keratin compound prepared by reacting soluble keratin with formol to provide reactive moieties on the protein, and then removing excess formol. By pre-reacting formol with the soluble keratin, there is not a need to provide free formol in solution for reaction with hair. The formol concentration in the resulting formulation can be far below the levels in competitive products (ca. 2%) and well below recommended thresholds for cosmetic products, such as below about 1000 ppm, about 500 ppm, or about 200 ppm. The soluble keratin protein may be Tri-Ionic Keratin™, an ionized soluble protein marketed by Keratronics, Inc. (Coral Springs, Fla.), or other soluble keratin compositions having a molecular weight between about 12,000 and 19,000 daltons.

In another aspect, the present invention includes a system for treating damaged hair comprising:
a) application of the aforementioned formulation of the present invention to human hair to reduce cysteine bonds in the hair and thereby relax the hair;
b) application of heat to the hair to cause the ionized keratin derivative in the formulation to react with the hair, thereby becoming bonded to the hair, and to cause formation of disulphide bonds in the hair thereby permanently setting the hair; and
c) removing the remaining formulation from the hair.

In another aspect, the present invention includes a system for revitalizing hair comprising:
a) washing the hair of the subject;
b) drying the hair;
c) applying a formulation to the hair comprising an ionized reactive keratin derivative with a molecular weight range of about 12,000 to 19,000 daltons and comprising a plurality of reactive groups obtained by reaction of an aldehyde with a keratin compound, the formulation further comprising an oxidizing agent, an amino-functional silicone, and one or more additional silicone-based conditioning agents such as cyclo-dimethicone;
d) elevating the temperature of the formulation on the hair to cause the ionized keratin protein derivative to react with the hair, whereby the reaction repairs damaged regions of the cuticle and increases hair strength.

Without wishing to be bound by theory, it is believed that the silicone components such as aminopropyl phenyl trimethicone and an emulsion of water and cyclo-dimethicone can act as a barrier film on the hair shaft during application, holding the oxidants and the keratin protein complex in place. During hair treatment, the emulsion of the ingredients is evenly coated on all the hair shafts. Then, the emulsion is allowed to saturate the hair shaft for about 10 to 20 minutes, for example. During this process, the reactions of available aldehyde groups on the ionized keratin with sulfur groups sulfur on the proteins of the hair shaft occur, leading to film formation around the hair shaft. Slow polymerization reactions occur, driven by elevated temperature and the presence of oxygen or other oxidizers. Without wishing to be bound by theory, it is believed that the reaction of sulfur groups in the hair with reactive groups in the ionic keratin derivative result in strong covalent bonds holding a keratin film in place around the hair shaft, strengthening the hair, filling in defects, and sealing in other components of the formulation or byproducts thereof that may be released during heating of the hair. The amino-functionalized silicone compounds and other compounds present are also believed to form a coating that help seal the shaft, such that volatile compounds formed by reaction of the ionized keratin with the hair or other components are not readily released into the atmosphere, but are hindered from escaping by the keratinaceous film and the barrier-like properties of the silicone compounds and other ingredients.

In one aspect, the invention provides a system for hair-revitalizing products that do not require excessive oxidizing or bleaching chemicals. In certain aspects, the systems and formulations of the present invention are believed to differ over the prior art, among other things, in their mechanism for interaction with hair, whereby certain compounds are entrapped in the hair to prevent premature escape and thereby enable the compounds to further or more effectively revitalize the hair and bring it back to a full-bodied condition. In a similar manner, reconditioning and other forms of protection are provided in some embodiments of the present invention.

In another aspect, the present invention is directed to a hair revitalization treatment comprising application of a first composition comprising a keratin compound that is applied to the hair, wherein the keratin compound may comprise a solution or emulsion of an ionized keratin protein complex with film forming capability which is formed at elevated temperature to encase, restore, and protect the hair. In some embodiments, the use of hot irons and other tools in combination with the formulations of the present invention can provide permanent straightening of once highly curly, frizzy, or damaged hair as well as provide increased sheen and beauty to the hair.

Various embodiments of the present invention can be used to achieve a wide variety of advantages and benefits. In mentioning such advantages and benefits, in no way is it to be understood that such advantages and benefits are necessarily achieved by all embodiments of the present invention, and failure to achieve any one or more of the stated or implied advantages of benefits of any given embodiment in no way implies that an aspect of the invention is necessarily outside the scope of the invention as claimed. The advantages and benefits are for illustration only and not meant to provide limitations to the invention as claimed beyond the language of the claims themselves.

Among the advantages and benefits that can be achieved in some embodiments of the present invention are:

1. A hair-revitalizing and repairing solution and method hair treatment which does not expose hair to harsh chemicals such as oxidizing agents and high concentrations of aldehydes 2. A method of binding hair conditioning agents to the hair cuticle which does not scar the cuticle;

3. A hair revitalizing and repairing solution and method of treatment which traps effluents during ironing of the hair so that the effluents saturate the hair with chemicals which are trapped during treatment to prevent or hinder their release.

4. A hair revitalizing and repairing solution and method of treatment which employs a controlled polymerization reaction that increases the effectiveness and duration of a treatment relative to existing processes using high formol concentrations.

5. A hair revitalizing and repairing solution and treatment method which repairs damaged hair by filling recesses or notches in hair strands by bonding ionic-keratin protein to the hair protein via cross-linking with quinones and aldehyde groups.

6. A treatment solution and method which increases hair strand strain and yield strength by infusing the hair shaft with amino groups of an amino-functionalized silicone such and optionally other silicone fluids, which form a readily available deposition site for keratin protein molecules.

7. A solution and method which adds shine to hair using silicones and the phenol groups of aminopropyl phenyl trimethicone.

8. A controlled reaction site for polymerization of scented and non-scented aldehydes which then form covalent bonding sites for keratin sulfur groups such that a film of silicone forms an atmospheric battier for the reactants.

9. A treatment system comprising use of a formulation containing p-benzoquinone as an oxidizing agent for polymerization reactions, such that a controlled polymerization of aldehyde groups can be achieved without the release of substantial amounts of unreacted aldehyde molecules into the atmosphere.

10. A hair revitalizing and repairing solution and method of treatment which permits the user to swim and wash hair on the same day.

11. A solution and method for treating curly or damaged hair which is easy to use and practice and is safe and inexpensive.

BRIEF DESCRIPTION OF THE DRAWINGS

FIG. 2 shows a method of producing hydrolyzed keratin protein suitable for the present invention.

FIG. 4 shows an exemplary specific composition of a formulation according to the present invention.

FIG. 7 shows the effect on hair properties for several components of one embodiment of a formulation of the present invention.

DETAILED DESCRIPTION OF THE INVENTION

The Reactive Keratin Derivative

Figure 1:
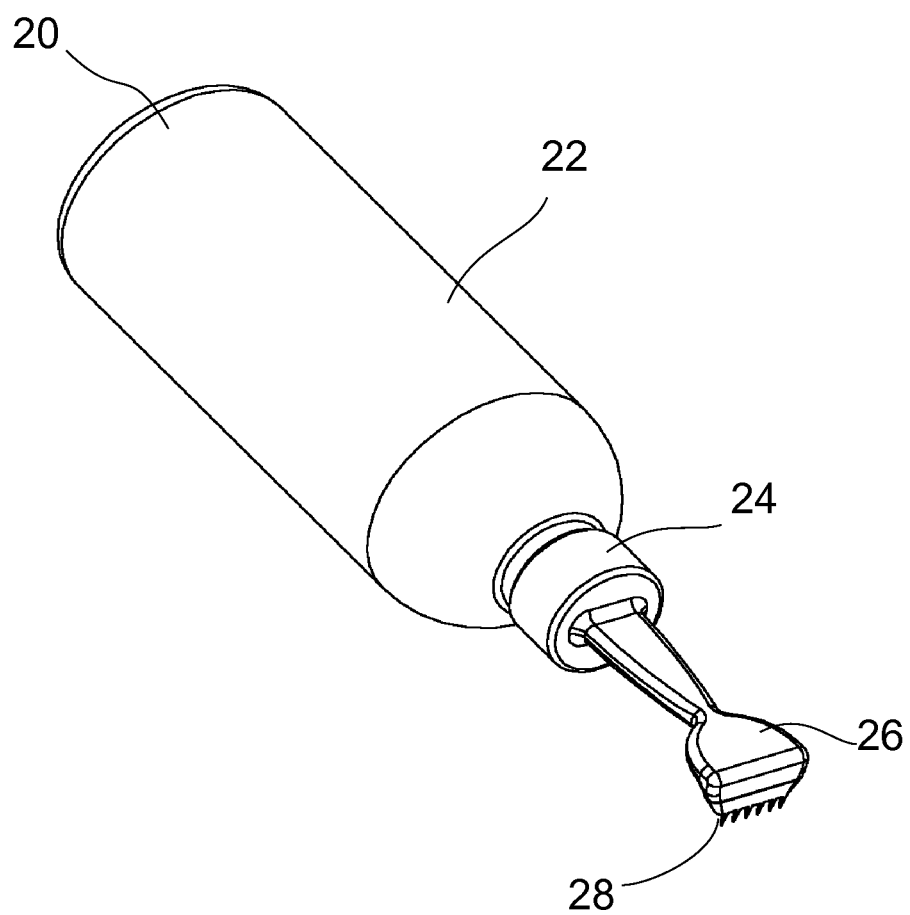
FIG. 1 shows a typical applicator bottle for the present invention with a comb dispenser.

The reactive keratin derivative of the present invention is a soluble keratin protein comprising a plurality of reactive aldehyde sites. Formation of the reactive keratin derivative comprises forming a soluble keratin compound such as hydrolyzing keratin protein, and further comprises addition of a plurality of reactive aldehyde groups to the keratin molecule. The resulting reactive keratin derivative is water soluble and ionized, and, in some embodiments directed toward hair straightening, is capable of participating in reactions with the keratin in hair in the presence of other ingredients in the formulation of the present invention both to promote initial reduction of disulphide bridges in hair to permit straightening of hair and to subsequently promote cross-linking reactions with the keratin in hair to bond the keratin to the hair for improved hair properties.

The method of producing the treatment solution involves the use of hydrolyzed α-keratin proteins which may be prepared, by way of example, according to the following steps:

a) preparing a keratin protein solution, such as a solution of ionized keratin derived from sheep wool or particularly alpine wool by any known process, such as that of U.S. Pat. No. 7,148,327, "Production of Soluble Keratin Derivatives," issued Dec. 12, 2006 to R. J. Kelly et al., herein incorporated by reference to the extent that it is noncontradictory herewith, which describes oxidative sulfitolysis for producing S-sulfonated keratin protein;

b) optionally heating and vaporizing the keratin solution to a fine mist;

c) hydrolyzing the keratin solution through the application of electric current;

d) adding an effective amount of a reactive aldehyde and optionally a catalyst to the hydrolyzed keratin protein solution under suitable conditions to promote the addition of reactive groups on the keratin protein, thereby forming a reactive keratin derivative.

In the solution comprising hydrolyzed keratin protein, the reactive aldehyde prior to reacting with the keratin may, for example, have an effective concentration of about 0.2% to 10% on a mass basis, such as from about 0.5% to 2% or from about 1% to about 1.5%.

The method may further comprise removal of excess reagents (e.g., removal of excess aldehydes and/or catalyst), sterilization by heat treatment or other methods, adjustment of the water content (e.g., dilution of the protein derivative to about 5 wt. percent to about 7-wt. percent in the solution), and fractionation of the reactive keratin derivative to a desired molecular weight range such as from 12,000 to 19,000 daltons. The resulting reactive keratin derivative solution may then be combined with other reagents to form a hair treatment formulation of the present invention.

The catalyst may comprise iron oxide or other metal oxides, noble metal particulates, and the like. Iron oxide and methanol, for example, may both be present in the ionized keratin solution in trace amounts, such as less than about 0.5% by weight, or less than about 0.1% by weight, respectively.

The current applied may be on the order of 200 amps per cubic meter and may be applied by any known method, such as by dielectric discharge between electrodes in the form of plates, rods, or other known structures.

The treated keratin solution may then be fractionated to obtain protein with a molecular weight range of from about 9,000 to about 25,000 daltons, or more specifically from about 12,000 to about 19,000 daltons. Fractionation may occur by use of membranes, electrophoresis, chromatography, reverse osmosis, and other known techniques. The fractionation may be done with a solution having a protein concentration of about 1% to 12%, such as from about 3% to 9%, or from about 6% to about 7%.

The keratin protein may comprise a keratin hydrolysate formed by any known method, such as that of U.S. Pat. No. 4,279,996, "Keratin Hydrolyzate Useful as Hair Fixatives," issued Jul. 21, 1981, U.S. Pat. No. 4,530,829, "Hair Treatments," WO06121700, "Hydratable Keratin Compositions," or GB526289A, "An Improved Process for Making Keratin Degradation Products Containing Calcium or Strontium and Gold," all of which are herein incorporated by reference to the extent that it is noncontradictory herewith. WO09000057A, "Keratin Hydrolysates, Process for Their Production and Cosmetic Composition Containing the Same" also teaches keratin hydrolysates of potential use within the scope of the present invention, as does US2001047082A, "Soluble Keratin Peptide," herein incorporated by reference to the extent that it is noncontradictory herewith. The keratin hydrolysate may comprise commercially available compounds such as the hydrolysate sold by Croda, Inc. (New York City, N.Y.) under the name "KERASOL", which is said to have an average molecular weight of about 125,000, typically provided in an aqueous solutions with about 15% protein and said to have film-forming capabilities. Other sources of soluble keratin products include Keratec (Lincoln, New Zealand) and Keraplast Technologies, Ltd. (San Antonio, Tex.). Other soluble keratin products are known under the CTFA adopted nomenclature as "soluble animal keratin" and generally have molecular weights greater than about 100,000.

Soluble keratin compounds for use in the present invention may also include those of U.S. Pat. No. 4,818,520, "Keratin Hydrolysate Formulations and Methods of Preparation Thereof," issued Apr. 4, 1989 to Fleischner, herein incorporated by reference to the extent that it is noncontradictory herewith. Fleischner discusses, for example, a method of preparing a neutralized viscous liquid proteinaceous extract comprising the steps of heating an aqueous mixture of keratin and alkaline material; refluxing said mixture for several hours at elevated temperature, thereafter cooling the refluxed solution and filtering said solution to recover a proteinaceous extract; adding acid; removing the precipitate formed during acidification of the extract by vacuum filtration; then heating and evaporating a portion of the resultant concentrated viscous filtrate; and adding alkali hydroxide to said viscous filtrate.

U.S. Pat. No. 5,679,329, "Cosmetic Composition for Holding the Hairstyle, Containing a Milk Protein and/or Milk Protein Hydrolysate and a Keratin Hydrolysate," herein incorporated by reference to the extent that it is noncontradictory herewith, also discusses compositions comprising a keratin hydrolysate. See also US2005232875, "Water-Soluble Keratin Derivative and Use Thereof," herein incorporated by reference to the extent that it is noncontradictory herewith. Principles for solubilizing natural proteins are also disclosed U.S. Pat. No. 5,460,967, "Recycle Process for the Production of Low-Cost Soluble Collagen," issued Oct. 24, 1995 to Fink and Brody, herein incorporated by reference to the extent that it is noncontradictory herewith.

The keratin protein complex may be a quaternary ammonium derivative of a keratin hydrolysate. Examples of methods for forming quaternary ammonium derivatives are given in U.S. Pat. No. 4,774,075, "Compositions Containing Bis-(Quaternary Ammonium) Derivatives for the Treatment of Keratin Materials and Natural Non-Keratin Materials or Synthetic Textile Materials," issued Sep. 27, 1988, herein incorporated by reference to the extent that it is noncontradictory herewith.

Addition of reactive groups to the keratin protein can be done by any known method, such as by reacting the keratin with formol, glutaraldehyde, or aldehydes, particularly low molecular weight aldehydes having, for example, less than carbons, wherein the aldehyde can be reduced in adding to or oxidizing disulfide bonds or thiol groups or other sulfur groups in the keratin. Subsequent oxidation of the added group can then provide aldehyde groups on the keratin.

The keratin protein complex may be obtained from any suitable source such as from mammal hair, hides, skin, plant sources, silk fibroin (an α-keratin) and synthetic sources. The protein in the protein complex may consist substantially of keratin derivatives, or may also comprise non-keratinaceous proteins such as those obtained from collagen or other animal or plant sources. For example, protein quaternary compounds may be used, such as those marketed by Croda, Inc. under the name "CROQUAT M" (cocoyl quaternized protein), also under the CTFA adopted name of "cocodimonium hydrolyzed animal collagen." Products formed by the hydrolysis of silk fiber may also be uses. For example, Croda, Inc. supplies a "CROSILK LIQUID" derived from silk.

The keratin need not be taken from a natural source, but may be synthesized or formed from recombinant biological methods, as described, for example, in US2001006664, "Recombinant Hair Treatment Compositions," herein incorporated by reference to the extent that it is noncontradictory herewith. The keratin may be carried as a payload in an emulsion of water with a hydrophobic phase such as cyclo-dimethicone, aminopropyl phenyl, trimethicone, and the like, further comprising a small fraction of substantially formaldehyde-free cross-linking agents, described below.

Silicone Compounds and Other Conditioning Agents

The formulation of the present invention comprises an amine-functional silicone to enhanced the interaction of conditioning agents with the hair. Amine-functional silicones can include aminopropyl phenyl trimethicone, amino bispropyl dimethicone, aminopropyl dimethicone, amodimethicone, and amodimethicone hydroxystearate. The amino groups of amino-functional silicones are particular useful in attaching the compound to damaged hair that has become relatively hydrophobic, thereby increasing the affinity of the hair for other conditioning agents. A variety of known conditioning agents can be added such as behenoxy dimethicone, C30-45 alkyl dimethicone, C24-28 alkyl dimethicone, C30-45 alkyl methicone, cetearyl methicone, cetyl dimethicone, dimethoxysilyl ethylenediaminopropyl dimethicone, hexyl methicone, hydroxypropyldimethicone, stearamidopropyl dimethicone, stearoxy dimethicone, stearyl methicone, stearyl dimethicone, vinyl dimethicone, and the like.

Non-silicone conditioning agents can include natural extractives and oils such as Jojoba oil extract, Vitamin E oil, emu oil, avocado oil, and the like. Fatty-acid derivatives maybe used such as poly-glyceryl laurates (e.g., poly-glyceryl-laurate 10), as well as related stearates, palmitate, oleates, and the like.

Oxidizers, Aldehydes, and Other Agents

Aldehydes can be present for purposes of providing fragrance and/or providing reactive groups that interact with the ionized keratin and keratin in the hair. The aldehydes may be substantially linear, acyclic, or cyclic (i.e., comprise ring structures, which may or may not be directly bonded to the formyl group of the aldehyde), and may have, for example 12 carbons or less, 9 carbons or less, or 6 carbons or less. Aldehydes such as citral, octanal, cinnamic aldehyde, and other known aldehydes may be used. Aldehydes other than formol may first be reacted with benzoquinone such as p-benzoquinone.

In some embodiments, the aldehydes may have one or two aldehyde groups, for example, and may have about nine or fewer carbons each, as exemplified by formol and glutaraldehyde. Excess aldehydes can be removed following reaction with the keratin such that the formulation of the present invention may be substantially formaldehyde free and substantially glutaraldehyde free. The formulation may have a formol and/or glutaraldehyde concentration of about 0.1% or less, about 0.05% or less, or about 0.02% or less, for example. Removal of aldehydes may be by any known process such as solvent extraction, distillation, catalytic reduction, reverse osmosis, reaction with urea or other reagents to form precipitates, and the like.

The oxidizers such as benzoquinone, other quinone derivatives including hydroquinone and aminoquinones (e.g., those of U.S. Pat. Nos. 4,023,926; 3,919,265 or 2,267,741), suitable peroxides, and the like, may participate in polymerization reactions similar to the tanning reactions known involving quinones and collagen or other proteins. Such oxidizers may thereby assist in the formation of a sealing layer around the hair shaft, participating with other aldehydes, the silicone fluids such as cyclo-dimethicone and amino-functionalized silicones, and sulfur groups from the ionized keratin derivative or the hair itself.

The silicone fluids remaining on the hair can impart shine and uniformity to the hair shaft.

Aminopropyl Phenyl Trimethicone marketed by Dow-Corning is believed to be specially formulated for hair reconditioning and straightening processes and is believed to comprise a blend of silicone copolymers both amino and phenyl functionality. The amino functionality enhances deposition on damaged hair while the phenyl group is believed to provide superior shine to the hair.

Among oxidizers, p-benzoquinone is both an excellent oxidizing agent and is also believed to assist in regulating polymerization with aldehyde groups as hair is exposed to elevated temperature during ironing, which in turn helps seal in any gaseous byproducts of reaction for slow release by diffusion to reduce exposure to hair stylists and others.

In some circumstances, it is believed that p-benzoquinone or hydroquinone can act on the amide groups of the amino-functionalized silicone such as aminopropyl phenyl trimethicone fluids to form strong cross links, strengthening the bonding of the ionized keratin to the hair and stabilizing the silicone compounds on the hair, thereby providing shine and luster that can last for many weeks. Further, p-benzoquinone, for example, is known to be a good stainer for many proteins, and thus, without wishing to be bound by theory, it is believed to be useful in stabilizing the died hair fiber with respect to a hair treatment with certain formulations of the present invention. For certain embodiments of the formulations of the present invention, the color of the formulation may be dominated by the combined effective colors of the keratin compounds employed and the p-benzoquinone, such that various shades of brown ranging from very dark hair up to creamy pink blond hair can be treated without affecting or staining the hair externally, since the staining agent will only penetrate and load the hair shaft while the silicone fluids remain as a coating on the outside cuticles. A rich variety of true hair colors may emerge in some treatments in such embodiment that enhance shine and strength to the hair. It is believed that the rapid formation of keratinous seals around the hair shafts can help prevents p-benzoquinone from changing the hair shaft externally or participating in extensive reactions with the keratin of the hair shaft itself.

Typically, the treatment methods of the present invention allow an operator or hair stylist to use the formulations of the present invention on treated hair without being subjected to undesirable fumes. The observed beneficial effects of the formulations of various embodiments of the present invention are believed to be due the film forming capabilities of the formulations of the present invention and/or the silicone-based compounds that are applied to the hair in conjunction with the film-forming keratin derivatives, such that undesirable agents, if produced from the aldehydes and keratin derivatives in the formulation during the treatment process when the hair is heated, are hindered from rapid release into the atmosphere.

The guar gum may include, for example, the cationic and other gums described in U.S. Pat. No. 6,306,377, "Hair Straightening/Smoothing Composition," issued Oct. 23, 2001 to L. S. Coppola and T. Ferullo, herein incorporated by reference to the extent that it is noncontradictory herewith.

Many other agents known in the art may be included in the formulations of the present invention. For example, additional reducing agents may be present, such as cysteamine and cysteine, or agents described in US2005013786A, "Hair Treatment Process for Smoothing the Hair," herein incorporated by reference to the extent that it is noncontradictory herewith.

DESCRIPTION OF THE DRAWINGS

Reference is now made to the drawings, wherein like characteristics and features of the present invention shown, in the various FIGURES are designated by the same reference numerals.

Referring to FIGS. 1-15, a production method is disclosed of formulating a keratin protein hair revitalizing and treatment solution, and a treatment method is further disclosed for repairing damaged hair using the treatment solution causing keratin bonding at damaged sites on hair strands.

FIG. 1 shows an applicator device 20 comprising a bottle 22 that holds a quantity of the formulation of the present invention. The bottle 22 is joined to a connector hear 24 which support and provide fluid communication with a comb dispenser 26 which may be used by a hair stylist or other operator to apply the formulations of the present invention to the hair of a subject. The teeth 28 of the comb dispenser may be used to comb applied formulation from the bottle 22 into the hair of the subject in a controlled manner.

FIG. 2 shows the steps of one embodiment of a method 30 for hydrolyzing keratin proteins for the formulation of the present invention. In this method 30, in a first step 32 keratin film protein (protein from keratin sources that may be useful in forming a film) is synthesized or chemically extracted from natural sources. In a second step 34 the protein is heated and vaporized in a fine mist. Heating may be, for example, to about 100° C. or higher, such as 110° C. to 150° C., and creation of the mist may be achieved by a nebulizer, atomizer, spray nozzle, and other means known in the art. In a third step 36, the vaporized keratin is then hydrolyzed using electrical current. The vaporized keratin may be coalesced back into a continuous aqueous phase prior to application of electrical current, or current may be applied across a gap to the droplets or particles of keratin entrained in steam or air. In the latter case, a spark gap, plasma or barrier discharge method may be used to deliver current across a flowing mist. In a fourth step 38, the aqueous mixture comprising keratin is then treated to obtain a faction of the keratin have a desired molecular weight range, such as from about 12,000 to about 19,000 daltons.

Figure 3:
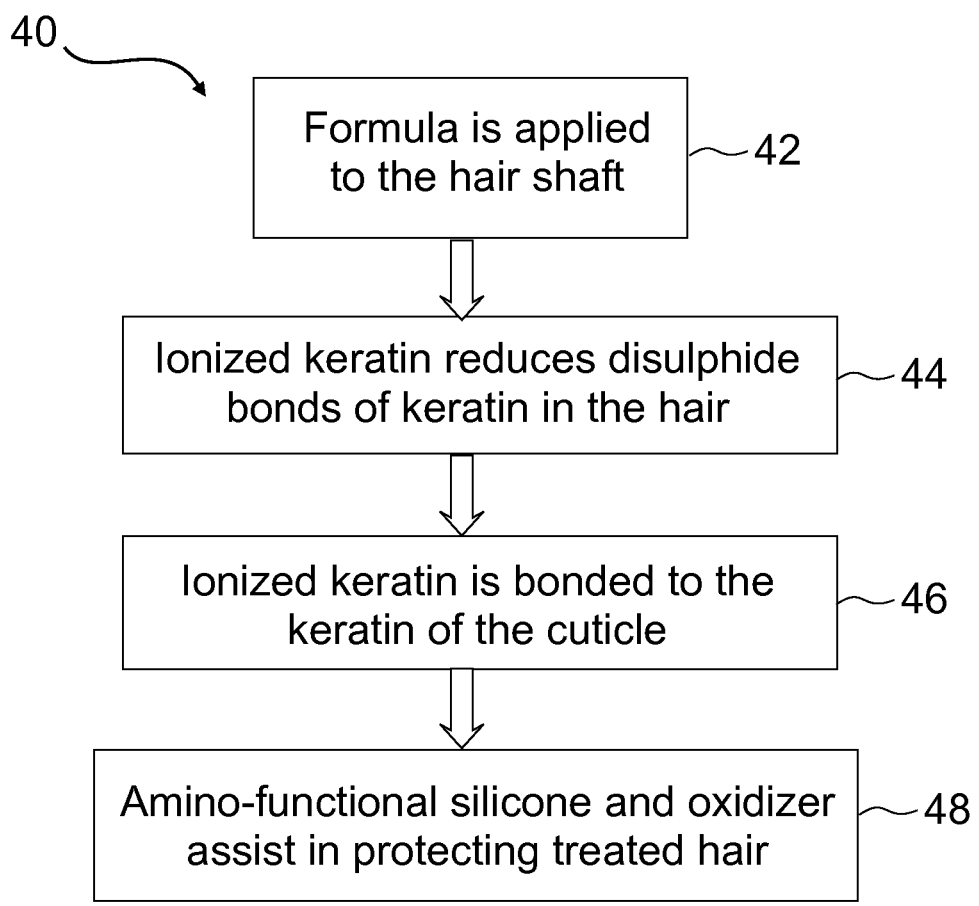
FIG. 3 shows the general hair cuticle penetration procedure for a hair treatment process according to the present invention.

FIG. 3 shows one embodiment of a method 40 for treating hair according to the present invention. In the method 40, in a first step 42, a formula containing reactive ionized keratin according the present invention is applied to the hair shaft of a user. In a second step 44, the reactive keratin interacts with some of the disulphide bonds in the hair of the user to reduce the disulphide bonds and thereby relax the hair, permitting curly or kinked hair to become relatively straighter. Without wishing to be bound by theory, it has been proposed that sulfonic, sulfonyl, or other sulfur-containing groups on the reactive keratin or otherwise in the formulation react with the disulphide groups in the keratin of the subject's hair to form reduced —SH groups. In a third step 46, the ionized keratin in the formulation is bonded to the keratin in the subject's hair, particularly the cuticle of the hair. This can result in increased strength and body, and may be manifest by increased tensile strength of the hair and increased strain prior to failure in mechanical testing. The yield or tensile strength of the subject's hair may increase by about 3% or more, such as by at least about 5%, 10%, or 15% or more as a result of the completed treatment. In a fourth step 48, which may occur substantially simultaneously with the third step in some embodiments, the amino-functional silicone and oxidizer interact with the hair and/or the ionized keratin to form a protective coating that helps to seal in the applied keratin and enhance the durability of the treatment.

FIG. 4 shows a table 50 providing an exemplary specific composition of a formulation according to the present invention. The Ti5 Trionic Modified Kerato-Protein Complex is a product derived from α-keratin from alpine wool marketed by Keratronics (Coral Springs, Fla.) which has been ionized and is believed to have been pre-treated with low-molecular weight aldehydes to provide reactive groups on the keratin backbone capable of further reacting with keratin in human hair.

Figure 5:
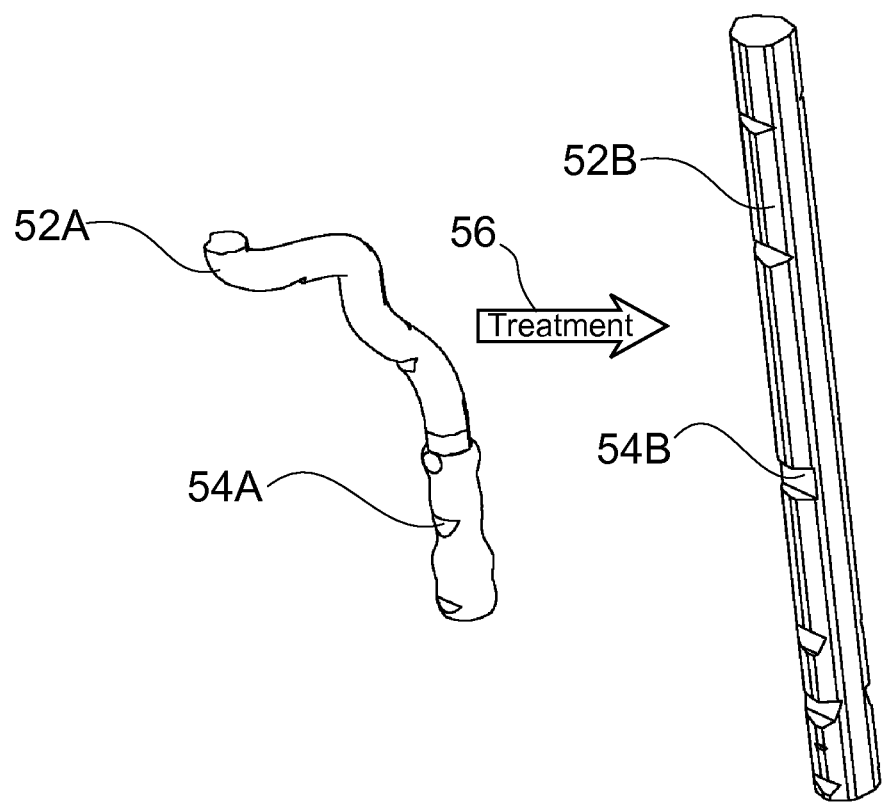
FIG. 5 illustrates how damaged areas of the cuticle open up to accept treatment when the hair is straightened using the system of the present invention.

FIG. 5 shows a curly hair strand 52A with a damaged section 54A, which, after undergoing the relaxation treatment 56 afforded by a formulation according to the present invention, becomes a relatively straight hair strand 52B with a damaged section 54B that is now relatively more open and thus more available for being filled in or strengthened by reaction with ionized reactive keratin. After the hair 52A is straightened, the damaged sections 54B of the hair 52B can better be repaired or strengthened under the present invention. FIG. 5 thus illustrates how a hair strand 52A, 52B with a damaged section 54A, 54B in the cuticle can open up to accept treatment when the hair 52A is straightened using the system of the present invention.

Figure 6:
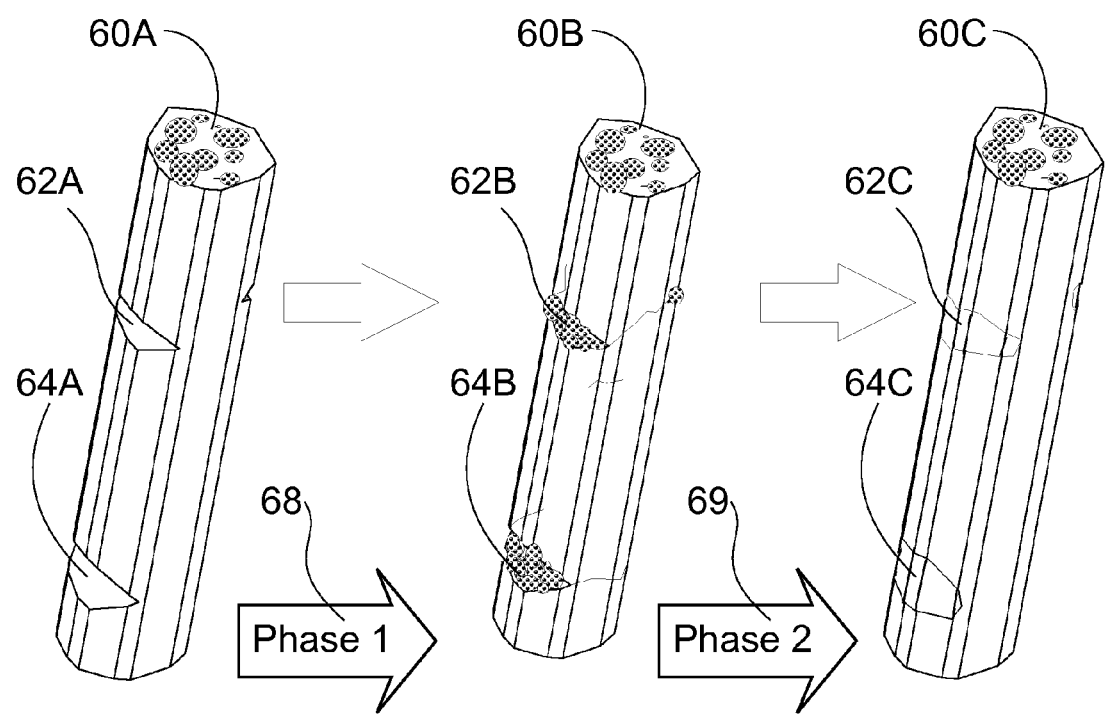
FIG. 6 illustrates how a treatment of the present invention causes keratin to bond with the damaged areas of hair to help repair the hair.

FIG. 6 depicts a damaged hair shaft 60A with damaged regions 62A, 64A. After being treated with the reactive ionized keratin of the present invention on Phase 1 68, the reactive ionized keratin has at least partially filled in or otherwise strengthened the damaged sites 62B, 64B that it has attached to on the treated shart 60B. In a second phase of the treatment, Phase 2 68, a hot iron is applied to the hair which permanently attaches the keratin and some of the silicone to the hair shaft 60C, resulting in substantially repaired damaged areas 62C, 64C. The hot iron can heat the hair shaft 60C to a suitable temperature to bond the reactive keratin to the hair shaft 60C and to also promote reaction of oxidizers and other components. Suitable temperatures may, for example, be about 350° F. or greater, such as from about 350° F. to about 450° F., or from about 360° F. to about 430° F., or from about 380° F. to about 420° F. The elevated temperature can result in reactions of the reactive ionized keratin and other components that form a protective film around the hair.

FIG. 7 shows a table 70 summarizing the effect on hair properties for several components of one embodiment of a formulation of the present invention. These effects are presented to illustrate some of the believed mechanisms achieved in some aspects of formulations of the present invention, but the theories presented or implicit in FIG. 7 and related discussions of apparent mechanisms are not intended to be limiting, and it is recognized that the complex interactions of the components of the formulation and the complex nature of human hair may result in actual mechanisms that differ from what is presently believed to occur.

Table 70 of FIG. 7 lists components in a first column 72, believed action of the respective components in a second column 74, and in a third column 76 the approximate increase in hair mass that may occur due to the contribution of interaction with the respective components. A fourth column 78 lists the torsional enhancement in hair properties that may occur due to interaction of the hair with the component or treatment in the first column 72.

Figure 8:
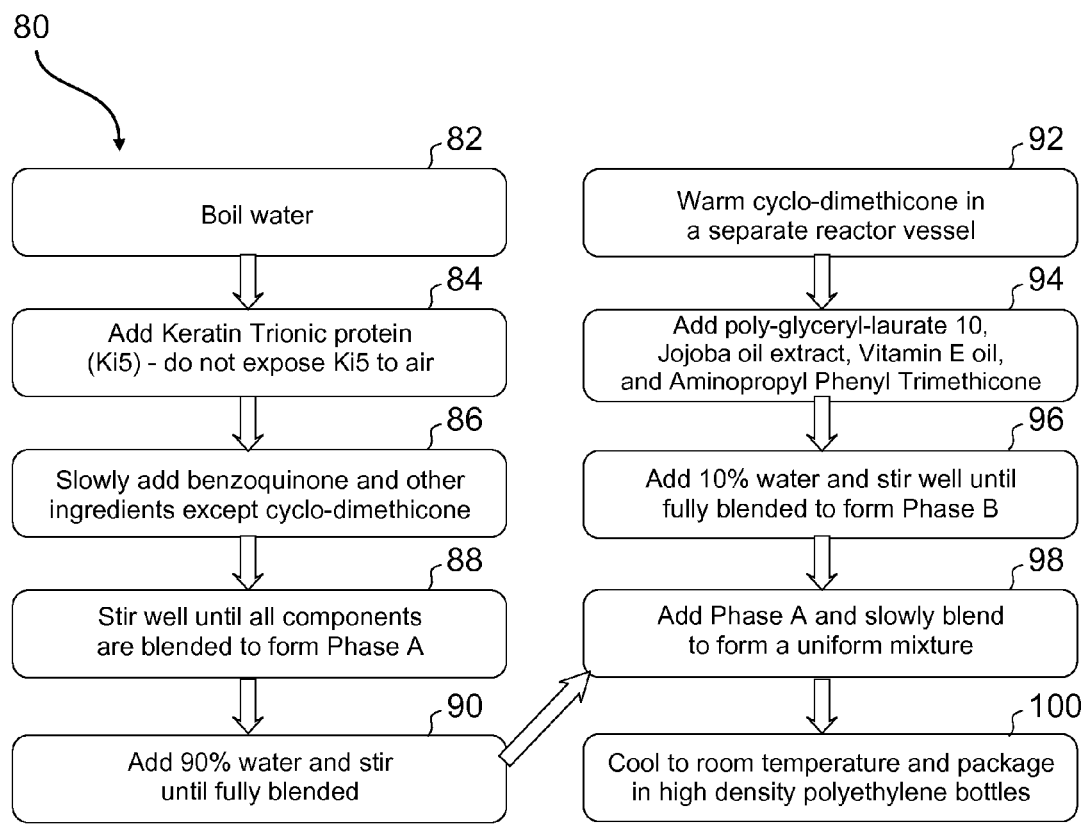
FIG. 8 shows the preparation flow chart for one embodiment of the formulation of the present invention.

FIG. 8 shows a method 80 of preparing one embodiment of the formulation of the present invention. First, water is boiled 82 to kill microbes. The water may be distilled, deionized water. Then the reactive ionized keratin protein, such as KI5 TRI-IONIC KERATIN™ of Kertatonics, Inc. (Coral Springs, Fla.) is added to a portion of the water 84. Combination of the reactive ionized keratin with the water may be done in a sealed chamber without to reduce exposure to air. Benzoquinone, cationic guar gum and other ingredients may be added (not cyclo-dimethicone and certain other ingredients, which are added later) 86. The guar gum may be slowly added in a manner to bring the solution to a viscosity of about 2000 centipoise, for example. The mixture is stirred until blended to form Phase A 88, and then Phase A is diluted with water 90. The portion of the boiled water used for making Phase A may be about 90% of the boiled water mass (the remaining portion may be reserved for subsequent blending with silicone compounds). In a series of steps that are carried out independently of steps 82-90, cyclo-dimethicone is warmed in a separate reaction vessel 92, and other miscible ingredients such as poly-glyceryl-laurate 10 or related compounds, Jojoba oil extract and Vitamin E oil or other oils, and aminopropyl phenyl trimethicone or other amino functional silicones 94. The respective proportions of ingredients may be selected according to the guidance given in FIGS. 4, 10, and 11. About 10% of the total boiled water may then added to heated cyclo-dimethicone mixture and stirred well until fully blended, thus forming Phase B 96. Phase A is added to Phase B (or visa versa, if desired) and slowly blended to form a uniform mixture 98. This can then be cooled to room temperatures and packaged in containers of any kind such as high-density polyethylene bottles 100.

Figure 9:
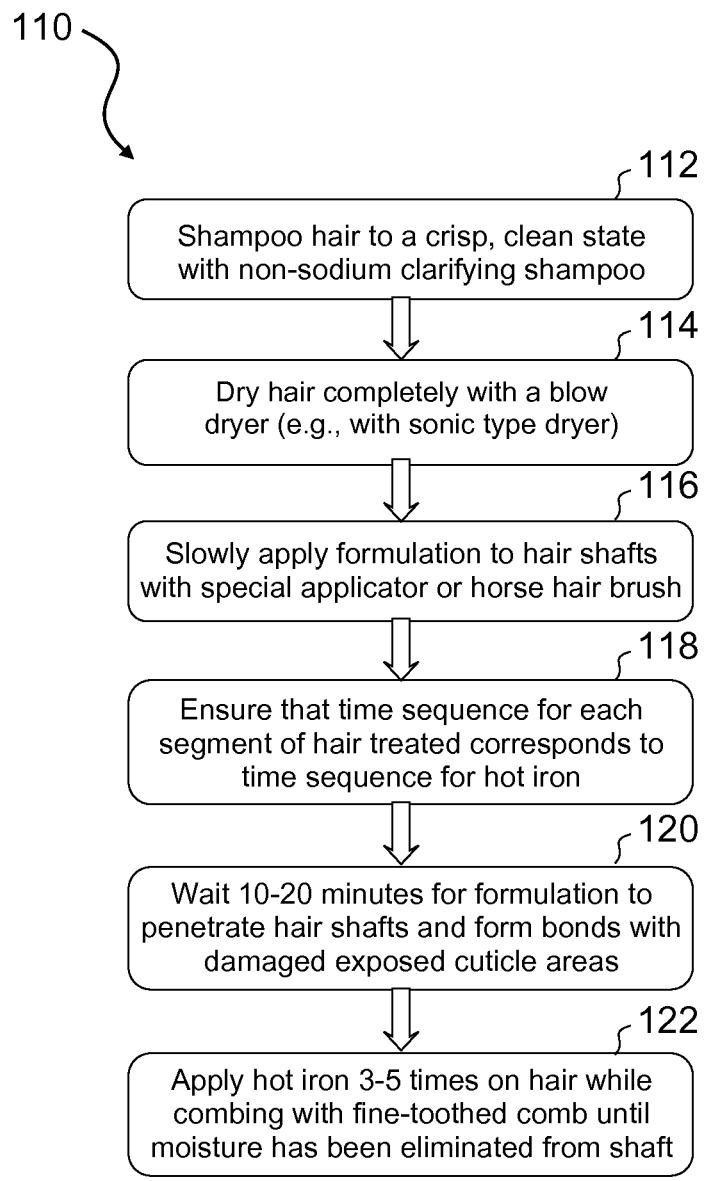
FIG. 9 shows an example of an application method for the formulation of the present invention to hair by a stylist in a salon.

FIG. 9 depicts an application method 110 for the formulation of the present invention to hair by a stylist in a salon. The method 110 begins with shampooing a subject's hair to a crisp, clean state using non-sodium shampoo or other suitable shampoos 112, followed by blow drying or otherwise drying the hair 114. A sonic dryer may be used. Then the stylist slowly applies the formula of the present invention to the hair shafts of the subject using an applicator such as that of FIG. 1, a soft horse hair brush, or other means 116. During application, the stylist should take care to ensure that the time sequence for treating each segment of the hair on the subject will correspond to the sequence used later in treating the hair with a hot iron 118. This may entail remembering or recording the order in which hair segments are treated. By so doing, better uniformity of treatment is achieved. After application, the stylist waits about 10 to 20 minutes to provide time for the formulation to penetrate hair shafts and form bonds with damaged portions of the cuticle of the hair 120. The stylist then applies a hot iron to segments of the hair 122, following the time sequence used in treating the hair with formulation. The hot iron may be applied several times, such as from 3 to 5 times, while also combing the hair with a fine-toothed comb. In this manner, further reactions occur to form permanent changes in the hair.

Figure 10:
FIG. 10 shows another embodiment of the formulation of the present invention.

FIG. 10 depicts a table 130 listing the composition for another embodiment of the formulation of the present invention.

Figure 11:
FIG. 11 shows another embodiment of the formulation of the present invention.

FIG. 11 depicts a table 140 listing the composition for yet another embodiment of the formulation of the present invention.

Figure 12:
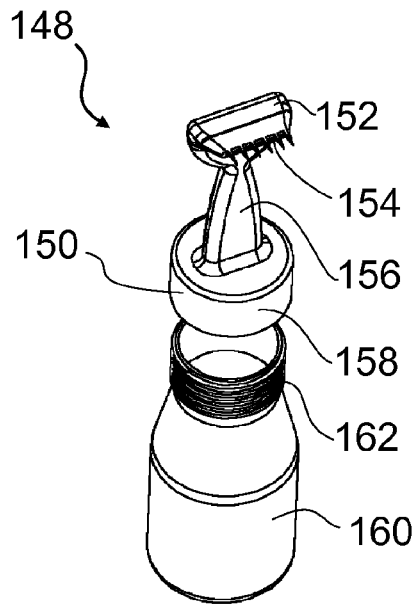
FIG. 12 shows an applicator bottle with a small sampler bottle and a professional use bottle for application of the formulation of the present invention.

FIG. 12 shows an applicator bottle 148 intended for use with a small sampler bottle 160 for holding a quantity of a formulation (not shown) of the present invention. The sampler bottle 160 comprises a threaded top portion 162 which can connect to a removable top portion 150 having an internally threaded base 158 (internal threads not shown), a shaft 156, and an applicator head 152 having comb elements 154. The applicator head 152 is in fluid communication with the formulation (not shown), allowing the contents of the sampler bottle 160 to be delivered to the applicator head 152 and the comb elements 154 thereof.

Figure 13:
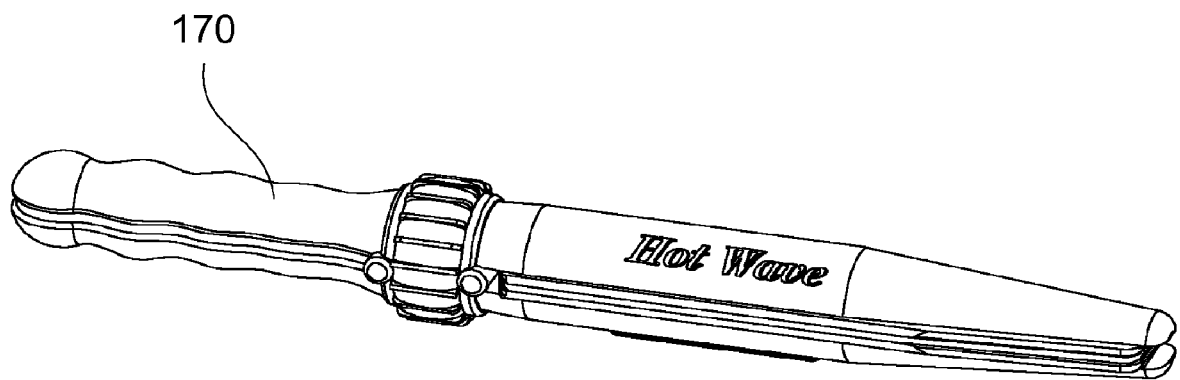
FIG. 13 shows an electric hot iron for performing one aspect of a treatment according to the present invention.

FIG. 13 shows an electric hot iron 170 for performing one aspect of a treatment according to the present invention. The hot iron 170 may be regulated to provide the desired temperature for effective reactions for the present invention.

Method of Repairing Damaged Hair with the Treatment Formulation

In one aspect of the invention, a hair treatment method is provided in which a formulation of the present invention is applied to the hair of a subject by an operator. In some embodiments, the method involves a general hair strand penetration procedure, including the steps of:

a) washing the hair thoroughly once or twice with a shampoo product, preferably a sodium free shampoo;

b) towel drying the hair, then blow-drying hair completely dry;

c) applying a solution comprising a formulation of the present invention such as one according to one of the exemplary formulations described in FIGS. 4, 10 and 11, using a fine toothed comb or an application brush for easy spreading;

d) permitting an ionized α-keratin protein derivative to react with sulfide bonds of the keratin structure of hair (without wishing to be bound by theory, this reaction may involve reduction of disulphide bonds by interaction with sulfonyl groups on the ionized keratin derivative, similar to the general reaction sequence $RSSR+HSO_3 \rightarrow RSH+RSSO_3$) and permitting the keratin protein and aldehydes to penetrate and bond to hair strands to repair or strengthen the hair;

e) leaving the solution on the hair for 10 to 20 minutes or as desired based on the operator's experience;

f) hot-ironing the hair using an electric heating iron, for example, to raise the temperature of the reactants and the hair strands to about 300° F. or greater and less that about 450° F., such that the reactants polymerizing into a long-lasting, pliable film of keratinous compounds around the hair strands, such that gaseous products if formed do not readily escape into the atmosphere.

As set forth in FIG. 9, a hair treatment method of the present invention may comprise the steps of:

a) shampooing hair with a non-sodium shampoo to an oil-free and clean condition;

b) completely or partially drying the hair with a blow-dryer or an ionic type hair dryer;

c) gradually applying a formulation of the present invention, such as one of those prepared according to FIG. 4, 10, or 11, to the hair strands of the user using an applicator such as of a brush applicator or a soft brush such as a horse hair brush, d) while applying the solution, ensuring that the sequence for treating each segment of the hair of the user is noted such that the sequence used in treating the subject's hair can also be used again in subsequently heating the hair of the subject;

e) waiting at least 15 minutes for the formulation to penetrate the hair strands and form bonds with damaged exposed areas;

f) heat hair strands to a temperature of at least about 375° F. but less than about 450° F. using a hot iron, or other heating means, using a sequence substantially the same as the sequence observed in Step D in applying the solution, and g) removing excess formulation from the hair.

The application of the formulations of the present invention may be enhanced with any known methods in the art, such as the use of ultrasound to better deliver reagents or complete reactions. Methods of using ultrasound for hair treatment, which may be adapted for the present invention if desired, include those disclosed in US2003106564A, "Method for the Ultrasonic Treatment of Hair and Other Keratinous Fibers," herein incorporated by reference to the extent that it is noncontradictory herewith.

Keratin from wool, quills and hair, and the like, contains low-sulfur proteins with high glycerin tyrosine proteins. Keratin matrices absorb water, and thus, it is generally desirable that hair strands be substantially dry prior to application of the formulations of the present invention. Without wishing to be bound by theory, it is believed that in the treatments of the present invention, a multi-phase protein structure is present wherein keratin protein, water, p-benzoquinone, glycerin tyrosine, amino-acids, and aldehydes form a protein complex in multi-phase form. The combination of microfibril matrix proteins and the water present in the cortex act to modify the stress and strain capabilities of the hair. Thus, the electrical conductivity of the keratin protein in the hair and in the treatment solution depend on the water content and the ionic character of the keratin molecules. Charged component interchange between the water molecules and the keratin proteins result in a rapid exchange of sulfur bonds which bind additional keratin from the treatment solution to the hair by covalent bonds. When excess water is evaporated by drying, interstitial bonding between keratin proteins takes place, until the hair strand is saturated with keratin product. The heat generated by ironing the hair then polymerizes the keratin as sulfur groups bind with aldehydes or other reactive groups, sealing keratin proteins in place and reducing the rate of release of gases produced in the reactions at elevated temperature during the treatment process.

Business Model Considerations

The products of the present invention may be distributed and marketed in any known manner. In some embodiments, however, marketing and use of the formulations of the present invention is carried out in professional salons. For example, both bottles of the formulation and special applicators for applying the formulation, exemplified by FIGS. 1 and 12, may be provided exclusively or non-exclusively to professional salons. Samples of the product, include small sample-size bottles, may be provided, or larger kits may be provided. Salons receiving sample kits may test the product and then place orders for standard kits. New or existing client salons and other professionals may also request training to ensure that proper techniques are used for best results. Training may include videos in DVD or other formats to demonstrate techniques and benefits, multimedia content on Webs sites, live demonstrations, videoconferences, etc. In some embodiments, professional training may be provided in combination with a certification service, such that professional hair stylists an receive a certification of professional efficacy to verify that they have been properly trained.

In addition to offering training for professionals using the product, educational broadcasts may also be provided to educate the public about the benefits and characteristics of the treatment.

Naturally, products and services of the present invention can be provided in a wide variety of business models and formats, alone or in combination. Products and services may be provided and distributed through salons, retail outlets, direct marketing, etc. Accessories and supplemental products such as brushes, applicators, conditioners, shampoos, hair irons, cosmetics, jewelry, apparel, and the like may be provided with or without products of the present invention or in conjunction with products of the present invention, and may be provided individually, in kits and other assortments, etc. Products may also be customized for individuals by providing user-selected colors, scents, and other additives, which may be customized on location for clients of salons or customized in a factory and shipped to customers, etc.

REMARKS

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above compositions, products, systems and methods without departing from the scope of aspects of the invention, it is intended that all matter contained in the above description shall be interpreted as illustrative and not in a limiting sense.

While the foregoing description makes reference to particular illustrative embodiments, these examples should not be construed as limitations. The inventive system, methods, formulations and devices can be adapted for many other uses not explicitly listed above, and can be modified in numerous ways within the spirit of the present disclosure. All elements shown, for example, may be subject to a wide variety of enhancements and variations in packaging, indicia and printed instructions, dispensing, appearance, fragrance, texture, and so forth without departing from the scope of the present invention. Thus, the present invention is not limited to the disclosed embodiments, but is to be accorded the widest scope consistent with the claims below.

We claim:

1. A formulation useful for revitalizing hair comprising a reactive ionized keratin derivative in an aqueous solution, said reactive ionized keratin derivative comprising the reaction product of ionized keratin with a reactive aldehyde, the ionized keratin having a molecular weight between about 9,000 and 25,000 daltons, the formulation further comprising a silicone compound, one or more additional conditioning agents, and an oxidizer.

2. The formulation of claim 1, wherein the oxidizer agent comprises benzoquinone or a derivative thereof.

3. The formulation of claim 2, wherein the oxidizer comprises p-benzoquinone.

4. The formulation of claim 1, wherein the reactive aldehyde is selected from an aldehyde comprising one or two aldehyde groups and nine or fewer carbons.

5. The formulation of claim 4, wherein the reactive aldehyde is selected from formol and glutaraldehyde.

6. The formulation of claim 5, wherein the reactive aldehyde comprises formol, and wherein the formulation comprises less than 0.1% free formol.

7. The formulation of claim 1, further comprising an effective amount of a catalyst selected from a metal oxide and a noble metal.

8. The formulation of claim 1, wherein the ionized keratin has a molecular weight between about 12,000 and 19,000 daltons.

9. The formulation of claim 1, wherein the keratin derivative comprises ionized keratin that has been reacted with formol.

10. The formulation of claim 1, further comprising a thickening agent.

11. The formulation of claim 10, wherein the thickening agent is a cationic gum and wherein the formulation has a kinematic viscosity of between about 2000 and 5000 centistokes.

12. The formulation of claim 1, wherein the silicone compound comprises an amino functional silicone compound selected from the group consisting of aminopropyl phenyl trimethicone, amino bispropyl dimethicone, aminopropyl dimethicone, amodimethicone, amodimethicond hydroxysterate.

13. The formulation of claim 1, wherein the silicone compound comprises a cyclomethicone-dimethicone.

14. The formulation of claim 13, wherein the dimethicone comprises one or more of behenoxy dimethicone, C30-45 alkyl dimethicone, C24-28 alkyl dimethicone, cetyl dimethicone, dimethoxysilyl ethylenediaminopropryl dimethicone, hydroxypropyldimethicone, stearamidopropyl dimethicone, stearoxy dimethicone, stearyl dimethicone, and vinyl dimethicone.

* * * * *